United States Patent
Al-Khattaf et al.

(10) Patent No.: US 10,159,967 B1
(45) Date of Patent: *Dec. 25, 2018

(54) METHOD FOR MAKING A CATALYST AND CRACKING A HYDROCARBON STREAM TO FORM PROPYLENE/ETHYLENE

(71) Applicant: KING FAHD UNIVERSITY OF PETROLEUM AND MINERALS, Dhahran (SA)

(72) Inventors: Sulaiman Al-Khattaf, Dhahran (SA); Palani Arudra, Dhahran (SA); Amr Abdalla, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/135,691

(22) Filed: Sep. 19, 2018

Related U.S. Application Data

(63) Continuation of application No. 15/996,460, filed on Jun. 2, 2018, now Pat. No. 10,112,191, which is a
(Continued)

(51) Int. Cl.
*C07C 4/06* (2006.01)
*B01J 35/00* (2006.01)
(Continued)

(52) U.S. Cl.
CPC ........... *B01J 35/0086* (2013.01); *B01J 21/08* (2013.01); *B01J 29/40* (2013.01); *B01J 37/0221* (2013.01);
(Continued)

(58) Field of Classification Search
CPC ........ B01J 35/0086; B01J 29/40; B01J 21/08; B01J 37/0221; B01J 37/0244; B01J 37/08; C07C 4/06; C07C 2521/08; C07C 2529/40
See application file for complete search history.

(56) References Cited

U.S. PATENT DOCUMENTS

| 8,034,987 B2 | 10/2011 | Sekiguchi et al. |
| 2002/0082460 A1 | 6/2002 | Verduijn et al. |
| 2011/0009682 A1 | 1/2011 | Matsushita et al. |

FOREIGN PATENT DOCUMENTS

| CN | 101722025 B | 10/2011 |
| CN | 103418429 B | 12/2013 |

(Continued)

OTHER PUBLICATIONS

Eva Epelde, et al., "Modified HZSM-5 zeolites for intensifying propylene production in the transformation of 1-butene", Chemical Engineering Journal, www.sciencedirect.com/science/article/pii/S1385694714004926, vol. 251, Sep. 1, 2014, pp. 80-91 (Abstract only).

(Continued)

*Primary Examiner* — Brian A McCaig
*Assistant Examiner* — Jason Y Chong
(74) *Attorney, Agent, or Firm* — Oblon, McClelland, Maier & Neustadt, L.L.P.

(57) ABSTRACT

A method of producing propylene and ethylene from a butene-containing hydrocarbon stream by cracking olefin compounds in the butene-containing hydrocarbon stream in the presence of a core-shell ZSM catalyst, wherein the core-shell ZSM catalyst comprises a ZSM-5 core and a silica shell disposed thereon. Various embodiments of the method of producing propylene and ethylene, and the method of making the core-shell ZSM catalyst are also provided.

10 Claims, 4 Drawing Sheets

Related U.S. Application Data continuation of application No. 15/402,854, filed on Jan. 10, 2017, now Pat. No. 10,016,750.

(51) Int. Cl.
  *B01J 37/02* (2006.01)
  *B01J 21/08* (2006.01)
  *B01J 29/40* (2006.01)
  *B01J 37/08* (2006.01)

(52) U.S. Cl.
  CPC .......... *B01J 37/0244* (2013.01); *B01J 37/08* (2013.01); *C07C 4/06* (2013.01); *C07C 2521/08* (2013.01); *C07C 2529/40* (2013.01)

(56) References Cited

FOREIGN PATENT DOCUMENTS

| CN | 103539152 A | 1/2014 |
|---|---|---|
| CN | 102320912 B | 4/2014 |
| WO | WO 2016/017793 A1 | 2/2016 |

OTHER PUBLICATIONS

Xiangxue Zhu, et al., "Catalytic cracking of C4 alkenes to propene and ethene: Influences of zeolites pore structures and $Si/Al_2$ ratios", Applied Catalysis: A: General, http://www.sciencedirect.com/science/article/pii/S0926860X05002863, vol. 288, Issues 1-2, Jul. 15, 2005, pp. 134-142 (Abstract only).

W.Tong, et al., "Synthesis and Characterization of ZSM-5/Silicalite-1 Core-Shell Zeolite with a Flouride-Containing Hydrothermal System", Chinese Journal of Catalysis, https://www.researchgate.net/publication/286642444_Synthesis_and_Characterization_of_ZSM-5Silicalite-1_Core-Shell_Zeolite_with_a_Fluoride-Containing_Hydrothermal_System, vol. 29, Issue 12, Dec. 2008, pp. 1247-1252 (Abstract only).

Antoinette Lombard, et al., "Synthesis and characterization of core/shell Al-ZSM-5/silicalite-1 zeolite composites prepared in one step", Microporous and Mesoporous Materials, vol. 129, 2010, pp. 220-227.

Yi-Qiang Deng, et al., "Synthesis of HZSM-5@silicalite-1 core-shell composite and its catalytic application in the generation of p-xylene by methylation of toluene with methyl bromide", RSC Advances, vol. 4, 2014, pp. 37296-37301.

Mores et al. ("Core-shell H-ZSM-5/silicalite-1 composites: Bronsted acidity and catalyst deactivation at the individual particle level" Phys. Chem. Chem. Phys., 2011, 13, 15985-15994) (Year: 2011).

METHOD FOR MAKING A CATALYST AND CRACKING A HYDROCARBON STREAM TO FORM PROPYLENE/ETHYLENE

CROSS-REFERENCE TO RELATED APPLICATIONS

The present application is a Continuation of Ser. No. 15/996,460, now allowed, having a filing date of Jun. 2, 2018 which is a Continuation of Ser. No. 15/402,854, now U.S. Pat. No. 10,016,750 having a filing date of Jan. 10, 2017.

BACKGROUND OF THE INVENTION

Technical Field

The present invention relates to a method of producing propylene and ethylene from a butene-containing hydrocarbon stream by cracking olefin compounds present in the butene-containing hydrocarbon stream in the presence of a surface modified core-shell ZSM catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Propylene and ethylene are important compounds in chemical and petrochemical industries. They have been widely used to produce other useful compounds and polymers such as oxo alcohol, propylene oxide, cumene, methyl methacrylate, phenol, acrylic acid, isopropyl alcohol, acrylonitrile, oligomers, polyethylene, polypropylene, etc. A global propylene demand was estimated to be around 90 million tons in 2014, with an average annual growth rate of 4.6%.

The main sources of producing propylene in chemical and petrochemical industries are steam crackers or FCC units, wherein propylene is produced as a byproduct of cracking heavier fractions of a hydrocarbon feedstock. The amount of propylene that is coproduced in a steam cracker greatly depends on the composition of the hydrocarbon feedstock. However, with the recent decline in oil prices, cracking lighter hydrocarbons is no longer economically advantageous. The reduction of cracking lighter hydrocarbons may result in a reduction of producing propylene and ethylene. On the other hand, thermal cracking (or steam cracking), which is a large source of propylene production in refineries and chemical industries, may form a large amount of methane (a greenhouse gas) as a by-product.

Alternatively, several propylene production processes are also available as means for producing propylene. These processes include methanol-to-olefins (MTO), propane dehydrogenation, catalytic cracking of butenes, and olefins metathesis. Among these, butenes cracking has attracted attentions due to the availability of large and stable supplies of butene from FCC and steam cracking processes. Olefin Cracking Process (UOP-ATOFINA), Propylur (Lurgi), PCC process (Exxon-Mobil), SUPERFLEX® (Lyondell/Kellogg), and Mobil's Olefin Inter conversion Process (MOI) are examples of commercially available production processes for producing lower olefins such as ethylene and propylene via hydrocarbon streams containing $C_4$-$C_5$.

Modified zeolite catalyst has been studied for cracking reactions of butene to propylene and ethylene. For example, Rongrong Zhang et al. (Chinese Journal of Chemical Engineering, 2015, v. 23, pp. 1131-1137) prepared a silver modified HZSM-5 zeolite catalyst via ion exchange method, and further used the catalyst towards catalytic cracking of 1-butene. The maximum propylene yield was about 30% by mass and the activity of the silver modified HZSM-5 zeolite catalyst was found to be higher when compared to the parent zeolite. Furthermore, Jianwen Li et al. (Fuel Processing Technology 2015, v. pp. 32-38) reported that a HZSM-5 zeolite catalyst, which has been modified by phosphorus and/or iron, enhanced selectivity of the cracking reactions towards propylene formation. However, a gradual deactivation of the catalyst was observed in the phosphorus and/or iron modified catalyst. Accordingly, the butene conversion was dropped by about 20%, in the first 25 hours of butene cracking. In another study, Higuchi et al. (U.S. Pat. No. 9,205,415 B2) disclosed a process for propylene production using MFI or MEL-type catalyst having Si/Al atomic ratio of 500 to 1000. Effect of loading different alkali metal compound such as K, Na and Li were tested using dimethyl ether as feed. A propylene yield of about 27% by mole was observed when 1-butene was used as a feed. Moreover, Midorikawa et al. (U.S. Pat. No. 9,192,922) disclosed propylene production using ZSM-5 type catalyst modified with silica and phosphorous. The reaction was carried out in fluidized bed reactor with a feed having an ethylene to 1-butene weight ratio of 80:20. It was shown that after 3 hours of the reaction, the ethylene conversion was about 63.3% and the propylene yield was about 21.2%. In addition, Van Westrenen et al. (U.S. Pat. No. 8,822,749B2) disclosed mixed catalyst system having MFI (ZSM-5) and TON (ZSM-22) or MFI (ZSM-5) and MTT (ZSM-23) type molecular sieves for propylene production using dimethyl ether and 1-butene as a feed. Mixed catalyst system slightly enhances the propylene production when compared to single catalyst system. Besides, Al-Khattaf et al. (US Patent Application No. 2016/0130197 A1) disclosed a process for cracking $C_4$ olefins to propylene and ethylene via an MFI zeolite catalyst having a Si/Al molar ratio of 2000. It was shown that acid-treating or base-treating the catalyst increases the propylene production yield. The increased propylene yield after base-treating the catalyst may be due to an enrichment of silanol group in the catalyst. Knowing the above disclosure, however, there appear to be no report on utilizing a surface modified ZSM-5 as a cracking catalyst for the production of light olefins such as ethylene and propylene from a feed containing butene.

In view of the forgoing, one objective of the present invention is to provide a method of producing propylene and ethylene from a butene-containing hydrocarbon stream by cracking olefin compounds in the butene-containing hydrocarbon stream in the presence of a surface modified core-shell ZSM catalyst. Further embodiments of the present invention relates to methods of making the core-shell ZSM catalyst.

BRIEF SUMMARY OF THE INVENTION

According to a first aspect the present disclosure relates to a method of producing propylene and ethylene from a butene-containing hydrocarbon stream, involving contacting the butene-containing hydrocarbon stream with a core-shell ZSM catalyst to form a product stream comprising propylene and ethylene, wherein the core-shell ZSM catalyst includes a ZSM-5 core, and a silica shell having a thickness in the range of 0.5 to 50 m, which covers at least a portion of a surface of the ZSM-5 core.

In one embodiment, the core-shell ZSM catalyst is dispersed in a silica and/or an alumina binder.

In one embodiment, a weight percent of the silica shell in the core-shell ZSM catalyst is within the range of 4 to 75 wt %, with the weight percent being relative to the total weight of the core-shell ZSM catalyst.

In one embodiment, the core-shell ZSM catalyst has an acidity of less than 0.1 mmol/g.

In one embodiment, at least 50 wt % of the product stream is propylene and ethylene.

In one embodiment, a propylene-to-ethylene weight ratio of the product stream is within the range of 0.2 to 4.

In one embodiment, the method of producing propylene and ethylene from the butene-containing hydrocarbon stream further involves treating the core-shell ZSM catalyst with nitrogen at a temperature in the range of 400 to 700° C. prior to the contacting.

In one embodiment, the method of producing propylene and ethylene from the butene-containing hydrocarbon stream further involves mixing the butene-containing hydrocarbon stream with nitrogen to form a gaseous mixture prior to the contacting, wherein a partial pressure of the butene-containing hydrocarbon stream in the gaseous mixture is within the range of 5 to 50 psi.

In one embodiment, the butene-containing hydrocarbon stream is contacted with the core-shell ZSM catalyst a temperature in the range of 400 to 700° C., and a space velocity in the range of 800 to 10,000 $h^{-1}$.

According to a second aspect the present disclosure relates to a method of making a core-shell ZSM catalyst, involving i) treating a ZSM-5 zeolite with a silicalite gel including a silicating agent, a structure directing agent, a mineralizing agent, and water at a temperature in the range of 150° C. to 250° C. and a pressure in the range of 2 to 20 bars, ii) calcining the core-shell ZSM catalyst to form the core-shell ZSM catalyst having a silica shell with a thickness of 0.5 to 15 µm, iii) treating the core-shell ZSM catalyst with the silicalite gel, iv) repeating the calcining and the treating until the thickness of the silica shell is in the range of 0.5 to 50 µm.

In one embodiment, the core-shell ZSM catalyst is treated once but no more than three times.

In one embodiment, a weight percent of the silica shell in the core-shell ZSM catalyst is within the range of 4 to 75 wt %, with the weight percent being relative to the total weight of the core-shell ZSM catalyst.

In one embodiment, a ratio of an acidity of the core-shell ZSM catalyst to the ZSM-5 zeolite is no more than 0.2.

In one embodiment, the structure directing agent is a quaternary ammonium salt with a chemical formula $N(C_nH_{3n})_4^+X^-$, with X being a halide ion or a hydroxide, and n being an integer between 1 to 5.

In one embodiment, the mineralizing agent is a fluoride salt.

In one embodiment, the silicating agent is silica.

According to a third aspect the present disclosure relates to a method of making a core-shell ZSM catalyst, involving i) treating a ZSM-5 zeolite with a silicating solution comprising an organic solvent and a silicating agent at a boiling point of the organic solvent, ii) calcining the core-shell ZSM catalyst to form the core-shell ZSM catalyst having a silica shell with a thickness of 0.5 to 5 µm, iii) treating the core-shell ZSM catalyst with the silicating solution, iv) repeating the calcining and the treating until the thickness of the silica shell is in the range of 0.5 to 30 µm.

In one embodiment, the core-shell ZSM catalyst is treated once but no more than six times.

In one embodiment, a ratio of an acidity of the core-shell ZSM catalyst to the ZSM-5 zeolite is in the range of 0.45 to 0.65.

In one embodiment, the silicating agent is tetraethylorthosilicate and/or aminopropyltrimethoxysilane.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
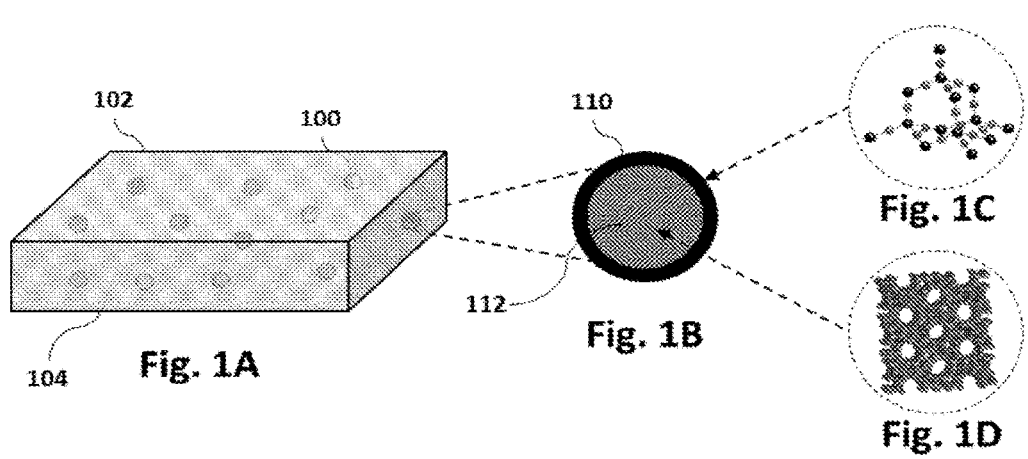
FIG. 1A illustrates a catalyst bed in the form of a matrix comprising a core-shell ZSM catalyst and a binder.
FIG. 1B is a magnified illustration of the core-shell ZSM catalyst having a ZSM-5 core and a silica shell.
FIG. 1C is a magnified illustration of the silica shell.
FIG. 1D is a magnified illustration of the ZSM-5 core.

According to a first aspect the present disclosure relates to a method of producing propylene and ethylene from a butene-containing hydrocarbon stream, involving contacting the butene-containing hydrocarbon stream with a core-shell ZSM catalyst to form a product stream comprising propylene and ethylene.

The term "butene-containing hydrocarbon stream" refers to a hydrocarbon stream that contains butene and may further include $C_{5-12}$ olefin compounds. The term "butene", as used here, refers to all isomers of butene, including 1-butene, cis-2-butene, trans-2-butene, and/or isobutylene (also known as 2-methylpropene). Preferably, at least 50 wt %, more preferably at least 60 wt %, even more preferably at least 70 wt % of the butene-containing hydrocarbon stream is butene, with the weight percent being relative to the total weight of the butene-containing hydrocarbon stream.

The term "olefin" as used here refers to unsaturated straight-chain hydrocarbons, unsaturated branched hydrocarbons, or cyclic olefins. In one embodiment, the butene-containing hydrocarbon stream further includes at least one raw material selected from the group consisting of $C_{1-12}$ hydrocarbons, such as for example $C_{1-12}$ normal paraffins, isoparaffins, cycloparaffins (i.e. naphthenes), cycloparaffins having side chain alkyl groups, aromatics, and aromatics having side chain alkyl groups. For example, in one embodiment, the butene-containing hydrocarbon stream includes ethylene, propylene, 1-butene, cis- and trans-2-butene, pentene, hexene, methane, ethane, propane, butane, pentane, hexane, benzene, toluene, xylenes, and ethylbenzene. The butene-containing hydrocarbon stream may include at least 60 wt %, preferably at least 70 wt %, more preferably at least 80 wt % of $C_{4-12}$ olefin compounds, and preferably no less than 30 wt % of $C_{4-12}$ olefin compounds. A production yield of converting olefin to propylene and ethylene may not be considerable for a butene-containing hydrocarbon stream having an olefin content of less than 30 wt %.

In one embodiment, the butene-containing hydrocarbon stream may also include small quantities (i.e. less than 2 wt %, preferably less than 1 wt %) of oxygen-containing compounds (e.g. tert-butanol, methyl tert-butyl ether, methanol, etc). Further, the butene-containing hydrocarbon stream may include diolefin (diene) compounds e.g. propadiene, butadiene, and/or pentadiene. However, the diolefin compounds are highly polymerizable and may poison the core-shell ZSM catalyst, therefore a content of diolefin compounds may preferably be less than 1 wt %, preferably less than 0.5 wt %. In circumstances where the content of diolefin compounds is above 2 wt %, preferably above 5 wt %, the butene-containing hydrocarbon stream may be treated in a distillation or a partial hydrogenation unit to reduce the diolefin content down to less than 1 wt %, preferably less than 0.5 wt %.

In some embodiments, the butene-containing hydrocarbon stream may be a $C_{4-5}$ fraction of naphtha, which is isolated from products of thermal cracking of naphtha. The $C_{4-5}$ fraction may partially be hydrogenated to partially convert diolefins into olefins. The butene-containing hydrocarbon stream may be a $C_4$ fraction and a gasoline fraction isolated from products of fluidized catalytic cracking (FCC) of vacuum gas oil and other petroleum hydrocarbons. Alternatively, the butene-containing hydrocarbon stream may be a $C_4$ fraction and a gasoline fraction isolated from cokers. The butene-containing hydrocarbon stream may be a $C_4$ fraction and a gasoline fraction isolated from hydrocarbons synthesized by Fischer-Tropsch reaction (FT synthesis) from carbon monoxide and hydrogen. The butene-containing hydrocarbon stream obtained from these aforementioned sources may be used individually, or two or more may be used as a mixture. Alternatively, the butene-containing hydrocarbon stream may be an effluent of an ethylene cracker, a steam cracker, a separation column, or a combination thereof.

According to the method, the butene-containing hydrocarbon stream is brought into contact with the core-shell ZSM catalyst in a reactor to convert at least a portion of $C_{4-12}$ olefin compounds present in the butene-containing hydrocarbon stream to propylene and/or ethylene via a catalytic dealkylation reaction.

Contacting as used herein refers to a process whereby a liquid-state and/or a vaporized-state of a hydrocarbon-containing stream is directly contacted with a catalyst present in a catalyst bed of a reactor at reaction conditions that are favored for catalytic reactions to take place. Accordingly, in some embodiments, the butene-containing hydrocarbon stream is contacted with the core-shell ZSM catalyst by passing through the catalyst when in a liquid state, or by passing through and/or over the catalyst when in a vaporized-state (e.g. as an atmosphere to the catalyst). Additionally, the butene-containing hydrocarbon stream may be mixed with the core-shell ZSM catalyst to form a heterogeneous mixture. Among these, the preferred contacting is by passing the butene-containing hydrocarbon stream through the core-shell ZSM catalyst.

The reactor may be a cylindrical vessel that is vertically or horizontally oriented. Preferably the reactor is a vertically oriented cylindrical vessel, wherein the butene-containing hydrocarbon stream enters the reactor from a top end when the feed is in a liquid state, and the butene-containing hydrocarbon stream enters the reactor from a bottom end when the feed is in a vaporized state (e.g. the gaseous mixture). The reactor may be a fixed-bed reactor, a moving-bed reactor, or a fluidized-bed reactor, wherein the core-shell ZSM catalyst is brought into contact with the butene-containing hydrocarbon stream. Preferably, the reactor is a fixed-bed reactor. In one embodiment, the reactor is filled with the core-shell ZSM catalyst, and the butene-containing hydrocarbon stream is contacted with the core-shell ZSM catalyst at suitable reaction conditions (e.g. at a temperature in the range of 400 to 700° C., more preferably 500 to 650° C., and at atmospheric pressure or a pressure in the range of 0.01 to 1 MPa, preferably in the range of 0.05 to 0.3 MPa), whereby at least a portion of the $C_{4-12}$ olefin compounds is converted to propylene and/or ethylene.

The catalyst bed may be a container with an internal cavity that is filled with the core-shell ZSM catalyst, and is disposed inside the reactor. Examples of the catalyst beds include, but are not limited to a hollow tube, a pipe, a duct, etc. In a preferred embodiment, the reactor is a cylindrical vessel with the catalyst bed located inside, wherein the butene-containing hydrocarbon stream is contacted with the core-shell ZSM catalyst present in the catalyst bed. The reactor may include one or more catalyst beds that are located in series, however, preferably, the reactor has only one catalyst bed. The reactor may have various geometries including spherical, conical, pyramidal, rectangular, or cubical geometries. In one embodiment, the reactor has a volume in the range of 0.01-10,000 L, preferably 1-1,000 L, more preferably 100-1,000 L. Further to the core-shell ZSM catalyst, inert materials may be present in the reactor bed, for example to moderate hot spots throughout the reactor bed. Preferably the inert material is clay, sand, and/or gravel. The inert material may also be silica and/or alumina. The inert materials may be in the form of balls or pellets to catch impurities and to assist in flow distribution of the reactants through the catalyst.

A catalytic dealkylation reaction (or dealkylation) refers to a chemical reaction whereby one or more alkyl groups (e.g. methyl, ethyl, propyl, butyl, etc.) are removed from a hydrocarbon compound, for example, dealkylation of methylethylbenzene to form toluene. Dealkylation generally takes place in the presence of a catalyst. Further to the dealkylation reactions, other unfavorable catalytic reactions such as transalkylation or disproportionation may take place in the reactor. Transalkylation refers to a chemical reaction through which one or more alkyl groups (e.g. methyl, ethyl, propyl, butyl, etc.) are transferred from one organic compound to another. For example, transalkylation of a mixture containing toluene and trimethylbenzene may lead to the formation of xylene. Furthermore, disproportionation refers to a redox reaction in which an organic molecule is reduced in a reduction reaction, and the similar organic molecule is also oxidized in an oxidation reaction, thereby forming two different products. For example, disproportionation of toluene may form benzene (via an oxidation reaction), and xylene (via a reduction reaction).

In one embodiment, the method of producing propylene and ethylene from the butene-containing hydrocarbon stream further involves treating the core-shell ZSM catalyst with nitrogen prior to the contacting. Accordingly, the core-shell ZSM catalyst is first heated to a temperature in the range of 400 to 700° C., preferably 450-650° C., more preferably about 550-600° C., preferably in a sub-atmospheric pressure. Thermal treatment of the core-shell ZSM catalyst at a sub-atmospheric pressure may improve the resistance of the core-shell ZSM catalyst against coking deterioration. Then nitrogen is purged over the core-shell ZSM catalyst an atmospheric pressure, preferably at a pressure in the range of 2-10 atm. In one embodiment, the core-shell ZSM catalyst is held isothermally for at least 6 hours, preferably at least 8 hours, more preferably at least 10 hours, while purging with nitrogen.

In a preferred embodiment, after the core-shell ZSM catalyst is treated with nitrogen, the butene-containing hydrocarbon stream is mixed with a dilution gas stream to form a gaseous mixture prior to contacting the butene-containing hydrocarbon stream with the core-shell ZSM catalyst. In this embodiment, the gaseous mixture is passed through and/or over the core-shell ZSM catalyst to increase a contact surface area between the gaseous mixture and the core-shell ZSM catalyst. Preferably, a partial pressure of the butene-containing hydrocarbon stream in the gaseous mixture is within the range of 5 to 50 psi, more preferably 10-50 psi, even more preferably 20-40 psi. In one preferred embodiment, the butene-containing hydrocarbon stream is mixed with the dilution gas stream in an upstream mixer, and prior to being delivered to the reactor. However, in one embodiment, the butene-containing hydrocarbon stream is mixed with the dilution gas stream inside the reactor. The dilution gas stream may be a nitrogen stream, a carbon dioxide stream, a helium stream, and/or a methane stream.

Preferably, the butene-containing hydrocarbon stream is contacted with the core-shell ZSM catalyst a temperature in the range of 400 to 700° C., more preferably 500 to 650° C., even more preferably 540 to 600° C. In addition, in another embodiment, the butene-containing hydrocarbon stream (or the gaseous mixture) is contacted with the core-shell ZSM catalyst at an atmospheric pressure or a pressure in the range of 0.01 to 1 MPa, preferably in the range of 0.05 to 0.3 MPa, more preferably 0.05 to 0.2.

Furthermore, the butene-containing hydrocarbon stream is contacted with the core-shell ZSM catalyst at a space velocity in the range of 800 to 10,000 h$^{-1}$, preferably 1,000 to 5,000 h$^{-1}$, more preferably 1,000 to 2,000 h$^{-1}$. The term "space velocity" refers to a ratio of the volumetric flow rate of the influent of a reactor to a volume of the reactor (or the catalyst bed volume). Space velocity indicates how many reactor volumes of feed (e.g. the butene-containing hydrocarbon stream) can be treated per unit time. For example, a reactor with a space velocity of 5 h$^{-1}$ is capable of processing a feed with a volume that is equivalent to five times the reactor volume in each hour. A contact time between the butene-containing hydrocarbon stream and the core-shell ZSM catalyst is preferably 30 seconds or less, more preferably 10 second or less.

The product stream, which egresses the reactor in a liquid form and/or in a vapor form, includes propylene, ethylene, and one or more of $C_{4-12}$ olefin/diolefin compounds (e.g. cis- and trans-butene, pentene, hexene, propadiene, butadiene, pentadiene, cyclopentadiene, dicyclopentadiene, etc.), $C_{1-12}$ hydrocarbons such as n-paraffins, i-paraffins, cycloparaffins, and aromatics (e.g. methane, ethane, propane, butane, pentane, cyclopentane, hexane, cyclohexane, benzene, toluene, xylenes, ethylbenzene, etc.), oxygen-containing compounds (e.g. tert-butanol, methyl tert-butyl ether, methanol, etc), nitrogen, hydrogen, water vapor, and carbon dioxide.

In a preferred embodiment, at least 50 wt %, more preferably at least 55 wt %, even more preferably at least 60 wt % of the product stream is propylene and ethylene, whereas less than 20 wt %, preferably less than 15 wt %, more preferably less than 10 wt % of the product stream includes $C_{1-12}$ paraffin compounds such as n-paraffins, i-paraffins, and cycloparaffins (e.g. methane, ethane, propane, butane, pentane, cyclopentane, hexane, cyclohexane). Accordingly, the product stream of this embodiment may also include less than 40 wt %, more preferably less than 35 wt %, even more preferably less than 30 wt % of $C_{4-12}$ olefin/diolefin compounds (e.g. cis- and trans-butene, pentene, hexene, propadiene, butadiene, pentadiene, cyclopentadiene, dicyclopentadiene, etc.), with the weight percent being measured relative to the total weight of the product stream. In another preferred embodiment, a propylene-to-ethylene weight ratio (or P/E ratio) of the product stream is within the range of 0.2 to 4, preferably 1.0 to 3.5, more preferably about 3.0.

In a preferred embodiment, the yield of formation of propylene and ethylene is in the range of 40-65%, preferably 45-60%, more preferably 45-55%, with the yield being measured as the total weight of propylene and ethylene produced relative to the total weight of the $C_{4-12}$ olefin compounds present in the butene-containing hydrocarbon stream. In a preferred embodiment, the product stream of this embodiment includes less than 35 wt %, more preferably less than 30 wt % of $C_{4-12}$ olefin compounds (e.g. cis- and trans-butene, pentene, hexene, heptene, etc.), and a portion of the product stream is recycled back to the reactor and reacted again to increase the yield of formation of propylene and ethylene. According to this embodiment, the yield of formation of propylene and ethylene may increase to a range of 50-80%, preferably 60-70%, with the yield being measured as the total weight of propylene and ethylene produced relative to the total weight of the $C_{4-12}$ olefin compounds initially present in the butene-containing hydrocarbon stream.

In a preferred embodiment, the yield of formation of propylene and ethylene stays within the range of 40-65%, preferably 45-60%, more preferably 45-55%, over a period of at least 50 hours, preferably at least 100 hours, more preferably at least 200 hours. However, in another embodiment, the core-shell ZSM catalyst may be deactivated via coking deterioration in the reactor, when the catalytic reactions are carried out for more than 200 hours. According to this embodiment, the core-shell ZSM catalyst can be regenerated by burning off the coke on the catalyst at a temperature of 400 to 700° C., in an atmosphere of air or a gaseous mixture of oxygen and an inert gas.

In one embodiment, the method in accordance with the first aspect further involves separating propylene and/or ethylene from the product stream. Accordingly, a concentration of the $C_{1-12}$ hydrocarbons such as n-paraffins, i-paraffins, and cycloparaffins (e.g. methane, ethane, propane, butane, pentane, cyclopentane, hexane, cyclohexane, etc.)

may be reduced to less than 2 wt %, preferably less than 1 wt %, more preferably less than 0.5 wt % via a stripping column. Stripping refers to a process whereby one or more components of a liquid stream (e.g. $C_{1-12}$ paraffin hydrocarbons) are removed by a vapor stream. Accordingly, a stripping column is a vessel, wherein a liquid phase is in direct contact with a vapor phase at a condition favorable for one or more components of the liquid phase to transfer to the vapor phase via a mass transport phenomenon. Exemplary stripping columns used herein may include, but are not limited to tray towers, packed columns, spray towers, and bubble columns. The product stream may further be processed to remove other substances present in the product stream, for example, $C_{4-12}$ olefin/diolefin compounds (e.g. cis- and trans-butene, pentene, hexene, propadiene, butadiene, pentadiene, cyclopentadiene, dicyclopentadiene, etc.), oxygen-containing compounds (e.g. tert-butanol, methyl tert-butyl ether, methanol, etc), nitrogen, hydrogen, water vapor, carbon dioxide, etc.

Referring now to FIGS. 1A, 1B, 1C, and 1D. The core-shell ZSM catalyst 100 includes a ZSM-5 core 112 and a silica shell 110 that covers at least a portion of the ZSM-5 core.

Zeolites are porous aluminosilicate minerals that occur in nature. Elementary building units of zeolites are $SiO_4$ and $AlO_4$ tetrahedra. Adjacent tetrahedra are linked at their corners via a common oxygen atom, which results in an inorganic macromolecule with a three-dimensional framework. The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages.

In one embodiment, the core-shell ZSM catalyst 100 has a zeolite core, which is at least one zeolite selected from the group consisting of a 4-membered ring zeolite, a 6-membered ring zeolite, a 10-membered ring zeolite, and a 12-membered ring zeolite. The zeolite catalyst may have a zeolite with a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g. analcime, leucite, pollucite, and wairakite), phillipsite framework (e.g. harmotome), gismondine framework (e.g. amicite, gismondine, garronite, and gobbinsite), chabazite framework (e.g. chabazite-series, herschelite, willhendersonite, and SSZ-13), faujasite framework (e.g. faujasite-series, Linde type X, and Linde type Y), mordenite framework (e.g. maricopaite and mordenite), heulandite framework (e.g. clinoptilolite and heulandite-series), stilbite framework (e.g. barrerite, stellerite, and stilbite-series), brewsterite framework, or cowlesite framework. In one embodiment, the zeolite core is a zeolite selected from the group consisting of ZSM-5, ZSM-8, ZSM-11, ZSM-12, ZSM-18, ZSM-23, ZSM-35 and ZSM-39. Of these zeolites, the most desirable types of zeolites are those represented as MFI structures according to the IUPAC nomenclature for zeolite frameworks. For example, in a preferred embodiment, the core-shell ZSM catalyst 100 has the ZSM-5 core 112. ZSM-5 is an aluminosilicate zeolite belonging to the pentasil family of zeolites that has an MFI-type framework with a 10-membered ring structure. ZSM-5 is widely used in chemical, petro-chemical, and petroleum industries, for example as a heterogeneous catalyst for isomerization reaction of hydrocarbon compounds. Preferably, the ZSM-5 core 112 has a $SiO_2/Al_2O_3$ molar ratio in the range of 23-10,000, or preferably 23-2,000, or preferably 80-1,500, or preferably 200-400, or preferably about 300. To measure the $SiO_2/Al_2O_3$ molar ratio of the ZSM-5 core, the ZSM-5 core is dissolved in a strong aqueous alkali solution or a hydrofluoric acid solution, and the resulting solution is analyzed by plasma emission spectrometry, or the like to determine the $SiO_2/Al_2O_3$ molar ratio. The term "core" in the "ZSM-5 core" refers to the "zeolite core" in the "core-shell ZSM catalyst".

The ZSM-5 core 112 includes micro-pores (i.e. pores with an average pore diameter of less than 2 nm) having a specific pore volume in the range of 0.1-0.3 $cm^3/g$, preferably 0.1-0.2 $cm^3/g$, more preferably 0.15-0.2 $cm^3/g$. Preferably, an average pore diameter of the ZSM-5 core 112 is within the range of 4-12 Å, preferably 5-8 Å, more preferably 5-6.5 Å. The ZSM-5 core 112 may further include meso-pores (i.e. pores with an average pore diameters in the range of 2-50 nm, preferably 2-20 nm) having a specific pore volume in the range of 0.01-0.15 $cm^3/g$, preferably 0.05-0.15 $cm^3/g$, more preferably 0.05-0.1 $cm^3/g$. In one embodiment, a specific surface area of the micro-pores in the ZSM-5 core 112 is in the range of 100-500 $m^2/g$, preferably 300-500 $m^2/g$, more preferably about 400 $m^2/g$, whereas a specific surface area of the meso-pores in the ZSM-5 core 112 is in the range of 50-150 $m^2/g$, preferably 50-100 $m^2/g$, more preferably about 80 $m^2/g$. The core-shell ZSM catalyst 100 may be in the form of pellets having a diameter in the range of 0.5-5 mm, preferably 0.5-1.5 mm, more preferably about 1 mm. The core-shell ZSM catalyst 100 may also be extrudated to have a geometry selected from the group consisting of cylindrical, rectilinear, star-shaped, conical, pyramidal, rectangular, cubical, and ring-shaped.

In one embodiment, an acidity of the ZSM-5 core 112 is in the range of 0.01-2 mmol/g, preferably 0.1-1.5 mmol/g, more preferably 0.5-1.5 mmol/g. Alternatively, in another preferred embodiment, the ZSM-5 core includes substantially no protons. The term "containing substantially no protons" means that the amount of protons (i.e. the acidity) of the ZSM-5 core is 0.7 mmol or less, per each gram of zeolite. Preferably, the amount of protons is 0.01 mmol or less per gram of zeolite.

Zeolite catalysts having weak acid sites may be effective in catalyzing the formations of ethylene and propylene. On the other hand, zeolite catalysts having strong acidic sites may catalyze the formations of alkanes and aromatics. Forming a silica shell on the ZSM-core, as in the core-shell ZSM catalyst, protonates light olefin compounds to form carbocations thereby initiating acid-catalyzed reactions. The absence of strong acid sites in the core-shell ZSM catalyst may inhibit formed olefins (e.g. propylene or ethylene) to convert to alkanes or aromatics via hydrogen transfer reactions.

In one embodiment, a liquid phase ion exchange/filtrate titration method is used to determine an acidity of a zeolite. Accordingly, the acidity of the ZSM-5 core is measured as follows. First, the ZSM-5 core is calcined in air and then subjected to an ion exchange treatment in the presence of an aqueous sodium chloride solution. After the treatment, the solution is filtered to obtain a filtrate. The filtrate is washed with pure/deionized water, and the whole amount of the washing liquid is collected and further mixed with the aforementioned filtrate. The acidity of the resulting mixed solution (i.e. filtrate+washing liquid) is measured by neutralization titration, and a value per grams of the zeolite (i.e. the ZSM-5 core) is reported as the acidity of the zeolite (i.e. the ZSM-5 core). Alternatively, in a preferred embodiment, a temperature-programmed desorption (TPD) method is used to measure an acidity of a zeolite. Accordingly, a predetermined amount of the zeolite is pretreated at 500° C. in the presence of helium for at least 60 minutes, preferably 90 minutes. Then, the zeolite is treated at 100° C. in an atmosphere containing helium and 5 to 15 vol %, preferably 5 to 10 vol % of ammonia. After that, the zeolite is heated at a temperature ramp rate of 10° C. min$^{-1}$ from 100° C. to 600° C., wherein ammonia is desorbed, and the amount of desorbed ammonia (measured by a thermogravimetric analyzer) is used to determine the acidity of the zeolite.

In one embodiment, the ZSM-5 core 112 includes at least one transition metal selected from the groups 6-12 of the period table, such as V, Cr, Mo, W, Mn, Pt, Pd, Fe, Ni, Zn, Ga, and Re. Preferably, the transition metal is selected from the group 11 of the periodic table. Accordingly, the transition metal may be at least one selected from the group consisting of copper, silver, and gold. Of these metals, copper and silver are more preferred, wherein silver is the most preferred. In an alternative embodiment, the ZSM-5 core 112 may contain the transition metals in an oxide form. The transition metals may be incorporated into the ZSM-5 core via ion exchange, impregnation, and/or kneading, although the preferable method is ion-exchange. In order to incorporate a transition metal into the ZSM-5 core, the ZSM-5 core is treated in a metal salt, which may preferably be selected from the group consisting of silver nitrate, silver acetate, silver sulfate, copper chloride, copper sulfate, copper nitrate, and gold chloride. An amount of the transition metal in the ZSM-5 core may be in the range of 0.1 wt % to 5 wt %, preferably 0.5 wt % to 3 wt %, with the weight percent being relative to the total weight of the ZSM-5 core. In a preferred embodiment, the transition metals are evenly dispersed within the ZSM-5 core. The ZSM-5 core includes intra-crystalline and may also include inter-crystalline pores, and the transition metals may be located at the inter-crystalline pores or preferably at the intra-crystalline pores. In another embodiment, some or all of the aluminum atoms in the framework structure of the ZSM-5 core are replaced by atoms of Ga, Fe, B, and/or Cr.

Although, the silica shell 110 preferably covers a surface of the ZSM-5 core 112 entirely, in some alternative embodiments, the silica shell may cover at least 50%, or at least 80% of the surface of the ZSM-5 core. Preferably, the silica shell 110 has a thickness in the range of 0.5 to 50 μm, or preferably 5-40 μm, or preferably 10-30 μm, or preferably 15-30 μm.

A weight percent of the silica shell 110 in the core-shell ZSM catalyst 100 may depend on how the silica shell is formed on the ZSM-5 core, since the method of forming the silica shell on the core affects the thickness of the shell. For example, in one embodiment, the silica shell 110 is deposited on the ZSM-5 core 112 via a chemical liquid deposition method, wherein a weight percent of the silica shell in the core-shell ZSM catalyst is within the range of 4 wt % to 30 wt %, preferably 15 wt % to 30 wt %, even more preferably 15 wt % to 25 wt %, with the weight percent being relative to the total weight of the core-shell ZSM catalyst. Alternatively, in another embodiment, the silica shell 110 is deposited on the ZSM-5 core 112 via a hydrothermal method, wherein a weight percent of the silica shell in the core-shell ZSM catalyst is within the range of 4 to 75 wt %, preferably 30 to 75%, more preferably 50 to 75 wt %, with the weight percent being relative to the total weight of the core-shell ZSM catalyst. Each method of forming the silica shell on the ZSM-5 core is discussed in detail in the second and third aspect of the present disclosure.

The silica shell is configured to adjust the acidity of the core-shell ZSM catalyst 100 to be within a predetermined acidity by altering a thickness of the silica shell 110. The predetermined acidity may depend on how the silica shell is formed on the ZSM-5 core, since the method of forming the silica shell on the core affects the thickness of the shell. The method of forming the silica shell on the core may also affect the size of zeolite crystals of the ZSM-5 core. For example, in one embodiment, the silica shell 110 is deposited on the ZSM-5 core 112 via a chemical liquid deposition method, whereby a core-shell ZSM catalyst with a predetermined acidity in the range of 0.1-1 mmol/g, preferably 0.2-0.75 mmol/g is formed. In an alternative embodiment, the silica shell 110 is deposited on the ZSM-5 core 112 via a hydrothermal method, whereby a core-shell ZSM catalyst with a predetermined acidity of less than 0.1 mmol/g, preferably less than 0.05 mmol/g is formed. Each method of forming the silica shell on the ZSM-5 core is discussed in detail in the second and third aspect of the present disclosure.

As used herein, the term "silica shell" refers to a distinct silica coating/layer of the core-shell ZSM catalyst with a measurable thickness. In the embodiments where the catalyst is admixed with a binder (e.g. a silica binder) in the catalyst bed, the binder is substantially different than the silica shell (i.e. the binder such as a silica binder is entirely different from the silica shell, and is not considered as part of the core-shell ZSM catalyst).

Preferably, the propylene-to-ethylene weight ratio (or P/E ratio) of the product stream can be adjusted by varying the silica shell 110 thickness (and thus an acidity) of the core-shell ZSM catalyst 100. Furthermore, the P/E ratio of the product stream can be altered by altering the size of zeolite crystals of the ZSM-5 core. The P/E ratio adjustment of the product stream may be determined with respect to market or customer needs.

Referring now to FIG. 1A. In one embodiment, the core-shell ZSM catalyst 100 is dispersed in a binder 104 to form a matrix 102 including the binder 104 and the core-shell ZSM catalyst 100 dispersed therein. Accordingly, a porous, flame-resistant, inorganic oxide such as alumina, silica, zirconia, titania, diatomaceous earth, and/or clay may be mixed as the binder 104 with the core-shell ZSM catalyst 100 to obtain a catalyst mixture that can be molded to form the matrix 102. The matrix 102 can further be used as a catalyst bed in a reactor. According to this embodiment, the core-shell ZSM catalyst 100 is present in the matrix 102 with a weight percent in the range of 10 wt % to 90 wt %, preferably 20 wt % to 50 wt %, with the weight percent being relative to the total weight of the matrix.

According to a second aspect, the present disclosure relates to a method of making the core-shell ZSM catalyst, involving treating a ZSM-5 zeolite with a silicalite gel including a silicating agent (e.g. $SiO_2$), a structure directing agent, a mineralizing agent, and water.

Preferably, the ZSM-5 zeolite is calcined at a temperature in the range of 500 to 650° C., preferably about 550° C. before being treated with the silicating solution. The terms ZSM-5 zeolite and ZSM-5 core are used interchangeably herein.

In a preferred embodiment, the ZSM-5 zeolite is treated with the silicalite gel at a temperature in the range of 150° C. to 250° C., preferably about 200° C., and a pressure in the range of 2 to 20 bars, preferably 2 to 10 bars, more preferably 2 to 5 bars. The temperature and the pressure may be provided via an autoclave. Accordingly, the silicalite gel, which may be a suspension solution, is prepared first by mixing the structure directing agent, the mineralizing agent, and water. Next, a predetermined amount of the ZSM-5 zeolite is added to the silicalite gel having the silicating agent, the structure directing agent, the mineralizing agent and water. Preferably, a ratio of the silicating agent to the structure directing agent to the mineralizing agent to water is in the range of 0.5:0.05:0.1:15 to 1.5:0.1:2.0:25, more preferably about 1:0.08:1.6:20. A mineral acid, for example hydrochloric acid, may be added to the silicalite gel to adjust a pH to be within the range of 5-10, preferably 5-7. Further, the silicalite gel is sealed in the autoclave, which may preferably be made of stainless steel with a Teflonx liner, and the sealing is provided by metal end caps and temperature resistant rubber gaskets. The ZSM-5 zeolite is preferably treated with the silicalite gel to form a layer of silica on the ZSM-5 zeolite. Treating the ZSM-5 zeolite with the silicalite gel preferably refers to holding the ZSM-5 zeolite in the silicalite gel at a temperature in the range of 150° C. to 250° C., preferably about 200° C., and a pressure in the range of 2 to 20 bars, preferably 2 to 10 bars, more preferably 2 to 5 bars, for at least 1 day, preferably at least 5 days, more preferably at least 15 days.

After the treatment, the ZSM-5 zeolite is filtered and the filtrate is preferably washed with deionized water, followed by a drying at 80° C., preferably 70° C., for at least 1 day, preferably about 2 days. The dried ZSM-5 zeolite may further be calcined at a temperature in the range of 500 to 650° C., preferably about 550° C. to form the core-shell ZSM catalyst having a silica shell with a thickness of 0.5 to 15 μm.

In a preferred embodiment, the core-shell ZSM catalyst, which has already been calcined, is treated one more time, with a substantially similar treatment method to form another silica shell on the previously formed silica shell. Since the newly formed silica shell is indistinguishable from the former silica shell, and preferably no intermediate layer exists therebetween, the resulting catalyst after the second treatment may preferably be referred to as "the core-shell ZSM catalyst" having a silica shell with a thickness of 0.5 to 50 μm, preferably 5 to 50 μm, more preferably 10 to 40 μm.

The method of making the core-shell ZSM catalyst may involve repeating the calcining and the treating until the thickness of the silica shell is in the range of 0.5 to 50 m, preferably 5 to 50 μm, more preferably 10 to 40 m.

Preferably, the core-shell ZSM catalyst is treated at least once, but no more than three times. Accordingly, a core-shell ZSM catalyst that has been treated once may have an acidity in the range of 0.05-0.15 mmol/g, preferably about 0.1 mmol/g, whereas this quantity reduces to less than 0.01 mmol/g, when the core-shell ZSM catalyst is treated twice. In one embodiment, a ratio of the acidity of the core-shell ZSM catalyst to the ZSM-5 zeolite is no more than 0.2, preferably no more than 0.1, and no less than 0.01, preferably no less than 0.05, when the core-shell ZSM catalyst is treated twice.

In addition, the size of zeolite crystals of the ZSM zeolite in accordance with the method of the second aspect may be in the range of 2-5 μm, preferably 2-4 μm, more preferably about 3.5 μm.

In one embodiment, a weight percent of the silica shell in the core-shell ZSM catalyst, which is made in accordance with the second aspect, is within the range of 4 to 75 wt %, preferably 30 to 75%, more preferably 50 to 75 wt %, even more preferably about 65 wt %, with the weight percent being relative to the total weight of the core-shell ZSM catalyst.

In one embodiment, the structure directing agent is a quaternary ammonium salt with a chemical formula $N(C_nH_{3n})_4^+X^-$, with X being a halide ion or a hydroxide, and n being a positive integer between 1 to 5. Exemplary halide ions include but are not limited to, fluoride, chloride, bromide, and iodide. Accordingly, exemplary structure directing agents include but are not limited to tetramethylammonium hydroxide, tetraethylammonium hydroxide, tetrapropylammonium hydroxide, tetrabutylammonium hydroxide, tetrapentylammonium hydroxide, tetramethylammonium fluoride, tetraethylammonium fluoride, tetrapropylammonium fluoride, tetrabutylammonium fluoride, tetrapentylammonium fluoride, tetramethylammonium chloride, tetraethylammonium chloride, tetrapropylammonium chloride, tetrabutylammonium chloride, tetrapentylammonium chloride, tetramethylammonium bromide, tetraethylammonium bromide, tetrapropylammonium bromide, tetrabutylammonium bromide, tetrapentylammonium bromide, tetramethylammonium iodide, tetraethylammonium iodide, tetrapropylammonium iodide, tetrabutylammonium iodide, tetrapentylammonium iodide. In a preferred embodiment, the halide ion is bromide, and the structure directing agent is tetrapropylammonium bromide. In an alternative embodiment, the structure directing agent is cetyltrimethylammonium chloride, cetyltrimethylammonium bromide, cetyltrimethylammonium iodide, cetyltriethylammonium bromide, cetyltriethylammonium chloride, cetyltriethylammonium iodide, or any combination thereof.

In one embodiment, the mineralizing agent is a fluoride salt. The term "fluoride salt" refers to a chemical compound consisting of a cation and a fluoride anion. Preferably the fluoride salt is ammonium fluoride ($NH_4F$) and/or ammonium bifluoride ($NH_4HF_2$).

In an alternative embodiment, sodium hydroxide may be utilized as the mineralizing agent, as a replacement for the fluoride salt. Alternatively, sodium hydroxide may also be used in combination with ammonium fluoride ($NH_4F$) and/or ammonium bifluoride ($NH_4HF_2$).

Preferably, the silicating agent is silica ($SiO_2$), even though other silicating agents such as tetraethylorthosilicate (TEOS), tetramethylorthosilicate (TMOS), or polydimethylsiloxane (PDMS) may also be used individually or in combination with silica. Alternatively, sodium silicate, tetramethylammonium silicate, and/or sodium metasilicate may be utilized in conjunction with the silicating agent. In one embodiment, a weight ratio of the ZSM-5 zeolite to the silicating agent is in the range of 1:2, preferably 1:10, more preferably 1:25.

According to a third aspect, the present disclosure relates to a method of making the core-shell ZSM catalyst, involving treating a ZSM-5 zeolite with a silicating solution including an organic solvent and a silicating agent.

Preferably, the ZSM-5 zeolite is calcined at a temperature in the range of 500 to 650° C., preferably about 550° C. before being treated with the silicating solution.

In a preferred embodiment, the ZSM-5 zeolite is treated with the silicating solution at the boiling point of the organic solvent, which may be in the range of 50-120° C., preferably about 70° C., and at atmospheric pressure.

Accordingly, a predetermined amount of the ZSM-5 zeolite is mixed with the organic solvent. Exemplary organic solvents include, but are not limited to acetone, acetonitrile, chloroform, diethyl ether, dimethylacetamide, dimethylformamide, dimethylsulfoxide, isopropylalcohol, dioxane, ethanol, ethyl acetate, hexane, methanol, n-methylpyrrolidinone, pyridine, tetrahydrofuran, toluene, or a combination thereof. Preferably, the organic solvent is hexane with a boiling point of about 70° C.

The mixture of the ZSM-5 zeolite and the organic solvent is stirred, while concurrently heated until the temperature of the mixture reaches to the boiling point of the organic solvent. At this point, the organic solvent refluxes to the mixture, and a predetermined amount of the silicating agent (preferably about 4 wt %, relative to the total weight of the silicating solution) is added to the mixture, preferably in a dropwise manner, to form the silicating solution. The silicating solution is further stirred for at least 2 hours, preferably at least 5 hours, while the organic solvent is continuously refluxed at the boiling point of the organic solvent, whereby silica may start to deposit on the ZSM-5 zeolite, and the core-shell ZSM catalyst is formed. After that, the organic solvent may be removed from the silicating solution via vacuum evaporation, leaving behind the core-shell ZSM catalyst. After the treatment, the core-shell ZSM catalyst is filtered and the filtrate is preferably washed with deionized water, followed by a drying at 80° C., preferably 100° C., for at least 1 day, preferably about 2 days. The dried core-shell ZSM catalyst may further be calcined at a temperature in the range of 500 to 650° C., preferably about 550° C.

The core-shell ZSM catalyst produced via the method of the third aspect may have a silica shell thickness in the range of 0.5 to 5 µm. However, the core-shell ZSM catalyst, which has already been calcined, may be treated few more times, with a substantially similar treatment method to form one or more silica shells on the previously formed silica shell. Since the newly formed silica shell is indistinguishable from the former silica shell, and preferably no intermediate layer exists therebetween, the resulting catalyst after the last treatment may preferably be referred to as "the core-shell ZSM catalyst" having a silica shell with a thickness of 0.5 to 30 µm, preferably 5 to 30 µm, more preferably 5 to 25 µm.

Preferably, the core-shell ZSM catalyst is treated at least once, but no more than six times. Accordingly, a core-shell ZSM catalyst that has been treated once may have an acidity in the range of 0.1-1.5 mmol/g, preferably about 0.1-0.75 mmol/g, whereas this quantity reduces to less than 0.4 mmol/g, preferably less than 0.3 mmol/g, more preferably less than 0.2 mmol/g, when the core-shell ZSM catalyst is treated at least three time, preferably six times. In one embodiment, a ratio of the acidity of the core-shell ZSM catalyst to the ZSM-5 zeolite is in the range of 0.45 to 0.65, preferably 0.5 to 0.65, when the core-shell ZSM catalyst is treated six times.

In addition, the size of zeolite crystals of the ZSM zeolite in accordance with the method of the third aspect may be less than 2 µm, preferably less than 1 µm.

In one embodiment, a weight percent of the silica shell in the core-shell ZSM catalyst, which is made in accordance with the second aspect, is within the range of 4 wt % to 30 wt %, preferably 15 wt % to 30 wt %, even more preferably 15 wt % to 25 wt %/o, with the weight percent being relative to the total weight of the core-shell ZSM catalyst.

In a preferred embodiment, the silicating agent is silica ($SiO_2$), even though other silicating agents such as tetraethylorthosilicate (TEOS), tetramethylorthosilicate (TMOS), or polydimethylsiloxane (PDMS) may also be used individually or in combination with silica. Alternatively, sodium silicate, tetramethylammonium silicate, and/or sodium metasilicate may be utilized in conjunction with the silicating agent.

The examples below are intended to further illustrate protocols for the method of producing propylene and ethylene from a butene-containing hydrocarbon stream, and the methods of making the core-shell ZSM catalyst, and are not intended to limit the scope of the claims.

Example 1

The objective of the present disclosure is to modify ZSM-5 catalyst in order to improve ethylene and propylene yield from the catalytic cracking of I-butene. The modified ZSM-5 catalyst presented in this disclosure may be used in stand-alone units dedicated for the cracking of 1-butene or butene mixtures, which are produced from FCC crackers or ethylene crackers. The modified procedure involves a surface modification technique using silica by chemical liquid deposition method or core-shell silicalite composite synthesis. The present invention produces a higher yield of ethylene and propylene over prior catalysts with different P/E ratio. Additional objects, embodiments, and details of this invention can be obtained from the description of the invention.

Example 2

A method for surface modification of ZSM-5 catalysts in the cracking of I-butene to light olefins is provided. The MFI crystal structure with intersecting 10 membered-ring pore channels having a $SiO_2/Al_2O_3$ ratio (23, 80, 280 to 1500) were used for surface modification using chemical liquid deposition (CLD) method. In each cycle, 4 wt % of silica was deposited using tetraethylorthosilicate as the silica source. The number of silica deposition cycle on each material is described in Table 1. In each cycle of silica deposition, the acidity of the material was decreased as shown in Table 2.

TABLE 1

The catalysts used for catalytic cracking of 1-butene.

| Catalyst Code | Description |
|---|---|
| A | CBV 2314 from Zeolyst International calcined in air at 550° C. for 3 hrs. $SiO_2/Al_2O_3$ (mol/mol) = 23. |
| A1 | 3 times silica deposition using CLD method on catalyst A |
| A2 | 6 times silica deposition using CLD method on catalyst A |
| B | CBV 8014 from Zeolyst International calcined in air at 550° C. for 3 hrs. $SiO_2/Al_2O_3$ (mol/mol) = 80. |
| B1 | 3 times silica deposition using CLD method on catalyst B |
| B2 | 6 times silica deposition using CLD method on catalyst B |
| C | CBV 28014 from Zeolyst International calcined in air at 550° C. for 3 hrs. $SiO_2/Al_2O_3$ (mol/mol) = 280. |
| C1 | 3 times silica deposition using CLD method on catalyst C |
| C2 | 6 times silica deposition using CLD method on catalyst C |
| C3 | Silica deposition by core-shell synthesis using catalyst C |
| C4 | Silica deposition by core-shell synthesis using catalyst C3 |
| D | 890HOA from TOSOH Japan, calcined in air at 550° C. for 3 hrs. $SiO_2/Al_2O_3$ (mol/mol) = 1500 |
| D1 | One time silica deposition using CLD method on catalyst D |

TABLE 2

Results of temperature programmed desorption of ammonia (TPD) using parent and modified ZSM-5 catalysts.

| | NH$_3$-TPD (mmol/g) | | |
|---|---|---|---|
| Catalyst | >300° C. | 300-550° C. | Total Acidity |
| A | 0.46 | 0.29 | 0.75 |
| A1 | 0.31 | 0.16 | 0.47 |
| A2 | 0.28 | 0.14 | 0.42 |
| B | 0.27 | 0.13 | 0.40 |
| B1 | 0.21 | 0.11 | 0.33 |
| B2 | 0.12 | 0.09 | 0.21 |
| C | 0.08 | 0.07 | 0.15 |
| C1 | 0.07 | 0.05 | 0.12 |
| C2 | 0.06 | 0.04 | 0.10 |
| C3 | nd* | nd | nd |
| C4 | nd | nd | nd |

TABLE 2-continued

Results of temperature programmed desorption of ammonia
(TPD) using parent and modified ZSM-5 catalysts.

| Catalyst | NH$_3$-TPD (mmol/g) | | |
|---|---|---|---|
| | >300° C. | 300-550° C. | Total Acidity |
| D | 0.05 | 0.01 | 0.06 |
| D1 | nd | nd | nd |

*nd = not detectable

Example 3

Core-shell silicalite composite was synthesized using SiO$_2$/Al$_2$O$_3$ ratio 280. The parent material was mixed with gel composition of 1 SiO$_2$:0.08 TPABr:0.1-2.0 NH$_4$F:20 H$_2$O. The ratio of parent material and silica in the gel was about 1:2 (catalyst C3). Using sample gel composition, catalyst C3 was used as parent material for the synthesis of catalyst C4. The catalyst C3 and C4 show very weak acidic sites which well below the detection limit of TPD of ammonia analysis (Table 2). Weak acid sites act as an efficient catalyst for the formation of ethylene and propylene whereas strong acidic sites promote the formation of alkanes and aromatics. The acid sites on core-shell silicalite catalysts (Catalyst C3 and C4) are so weak and light olefins can easily be protonated to form carbocations. These weak acid sites may be able to form carbocations to initiate the acid-catalyzed reactions particularly at elevated temperatures (because the strength of acid sites increases with temperature). The absence of strong acid sites on the core-shell silicalite composite prevents the olefins from further conversion to alkanes and aromatics via hydrogen transfer reactions.

Example 4

The SEM images of catalyst C, 6 times silica deposited on catalyst C (C2), core-shell silicalite composite of the catalysts C3 and C4 was shown in FIG. 1. There was no change in morphology and crystal size of the catalysts C and C2. However, the crystal size of the catalysts C3 and C4 found to be about 2-3 μm larger than that of the parent zeolite (Catalyst C).

Example 5

The operating conditions of the 1-butene cracking reaction comprise temperatures between about 450° C. to about 700° C. A preferred temperature for operating the process is to be within the range from about 500° C. to about 650° C. with a more preferred operating temperature of about 540° C. to about 600° C. The reaction process operation conditions further include hydrocarbon partial pressures between about 35 kPa (5 psia) to about 345 kPa (50 psia). The catalytic process of 1-butene cracking can be conducted in a continuous circulating fluidized-bed reactor or in a fixed-bed reactor. The gas hourly space velocity (GHSV) based on 1-butene feed can be within the range 800 hr$^{-1}$ to 10000 hr$^{-1}$.

Example 6

The product yields of I-butene cracking over ZSM-5 catalysts comprise various hydrocarbon groups depending on the expected pathway to form different products. These groups are; 1-butene (reactant), cis- and trans-2-butene (double bond isomerization products), ethylene, propylene (target product), other olefins (pentenes, and hexenes) and n-butene isomers (skeletal isomerization and cracking products), alkanes (hydrogen transfer products), aromatics (benzene, toluene, xylenes and ethylbenzene; hydrogen transfer products), and C$_{8+}$ hydrocarbons (aromatics other than benzene, toluene, xylenes, and ethylbenzene, alkanes and olefins). Using modified ZSM-5 as the cracking catalyst for 1-butene may improve light olefin yields formation due to minimum side reactions such as isomerization and hydrogen transfer reactions, which lead to formation of C$_{8+}$ alkanes and aromatics.

Example 7—Silica Deposition Using Chemical Liquid Deposition Method

Silica coating on ZSM-5 zeolites with a different SiO$_2$/Al$_2$O$_3$ ratio of 23, 80 and 280 was carried out using chemical liquid deposition (CLD) method. Before silica coating zeolites material were calcined at 550° C. for 3 h with a heating rate of 5° C./min. In a typical coating procedure, 10 grams of parent zeolite was suspended in 100 ml of n-hexane solvent and the mixture was heated to the boiling point of n-hexane at 70° C., wherein n-hexane is refluxed. After 30 minutes of stirring and refluxing, a TEOS solution that corresponds to a loading of about 4 wt % SiO$_2$ was added and silylation was continued for 2 h at 70° C. with stirring and refluxing. Excess n-hexane was removed by evacuation. Finally, the sample was dried at 100° C. for 24 h and calcined at 550° C. for 4 h, with a heating rate of 5° C./min. After each TEOS deposition 2 g of catalysts were taken from a batch and subjected to physicochemical characterization and catalyst activity test. Silylation treatment was carried out up to six times using the same procedure.

Example 8—Synthesis of Core-Shell Composite ZSM-5(280) @ Silicalite-1 (1×) Catalysts (Catalyst C3)

HZSM-5(280) @silicalite-1 core-shell composite was prepared using tetra propyl ammonium bromide as structure directing agent and ammonium fluoride as a mineralizer. In a typical synthesis procedure, 6 g of ZSM-5 (280) zeolite was mixed well with silicalite-1 gel prepared using the following molar composition of the gel 1 SiO$_2$:0.08 TPABr: 1.6 NH$_4$F:20 H$_2$O. This was subjected to hydrothermal process at 200° C. for 2 days. The sample was then washed with deionized water, filtered, dried and calcined at 550° C. for 6 h.

Example 9—Core-Shell Synthesis of ZSM-5(280) Silicalite-1 (2×) Catalysts (Catalyst C4)

6 g of ZSM-5(280)(silicalite-1 was mixed well with silicalite-1 gel prepared using the following molar composition of the gel 1 SiO$_2$:0.08 TPABr:1.6 NH$_4$F:20 H$_2$O. This was subjected to hydrothermal process at 200° C. for 2 days. The sample was then washed with deionized water, filtered, dried and calcined at 550° C. for 6 h.

Example 10—Catalytic Performance of Modified ZSM-5 Catalysts

The catalytic performance of the modified ZSM-5 catalysts was evaluated in a fixed-bed packed with 2 ml of the catalyst with a particle size of 0.5-1.0 mm diameter. The catalyst sample was pretreated in a nitrogen stream at 550° C. for 1 h and then a mixture of the 1-butene and nitrogen (5 ml/min and 25 ml/min, respectively) (GHSV=900 h$^{-1}$) was passed through the catalyst bed at 550° C. The products were analyzed by an on-line gas chromatographer equipped with a GS-Gaspro column and a flame ionization detector (FID).

Example 11

Figure 2:
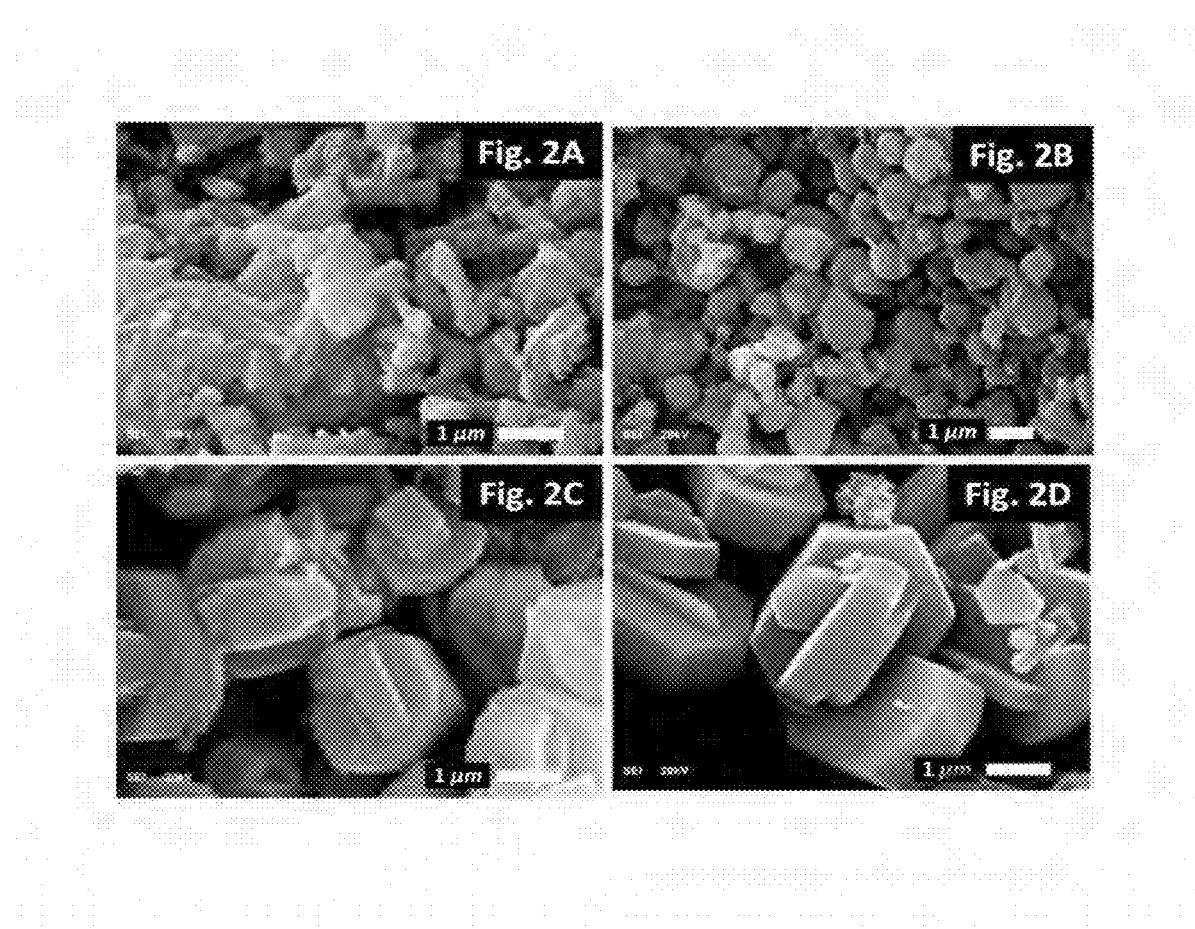
FIG. 2A is a SEM micrograph of a surface of the ZSM-5 core.
FIG. 2B is a SEM micrograph of a surface of the core-shell ZSM catalyst, which is made by treating the ZSM-5 core with a silicating solution six times.
FIG. 2C is a SEM micrograph of a surface of the core-shell ZSM catalyst, which is made by treating the ZSM-5 core with a silicalite gel, wherein zeolite crystals have a size of about 2 µm.
FIG. 2D is a SEM micrograph of a surface of the core-shell ZSM catalyst, which is made by treating the ZSM-5 core with a silicalite gel two times, wherein zeolite crystals have a size of about 3.5 µm.
Figure 3:
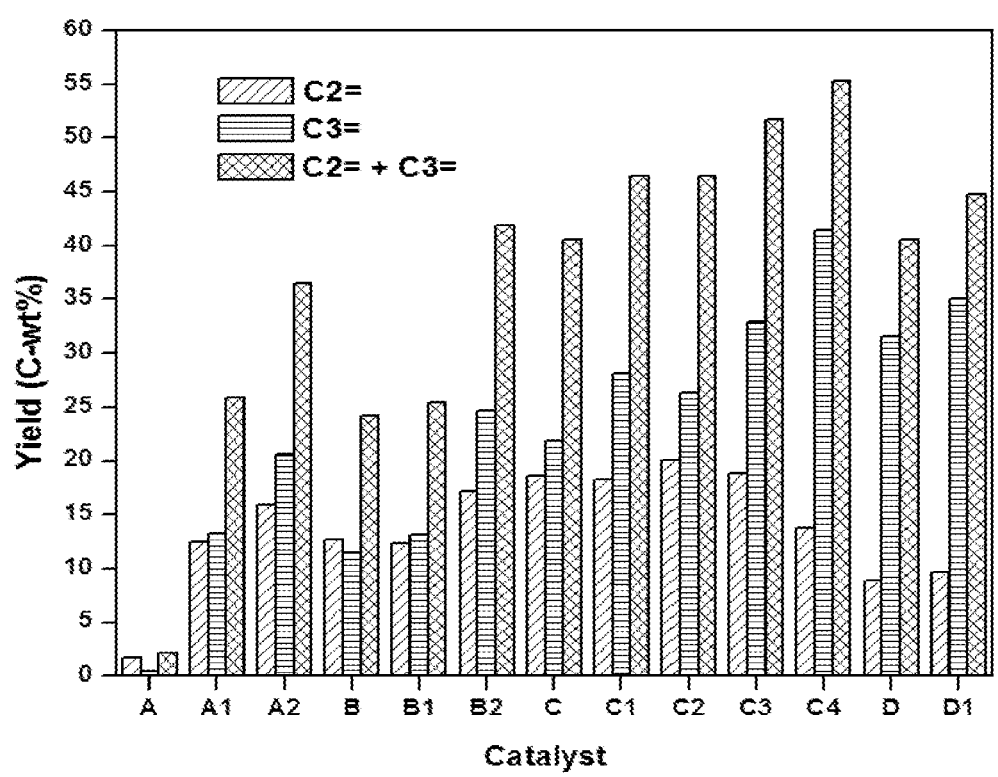
FIG. 3 represents a yield of cracking $C_{4-12}$ olefin compounds (e.g. butene) to ethylene and propylene via different catalysts.
Figure 4:
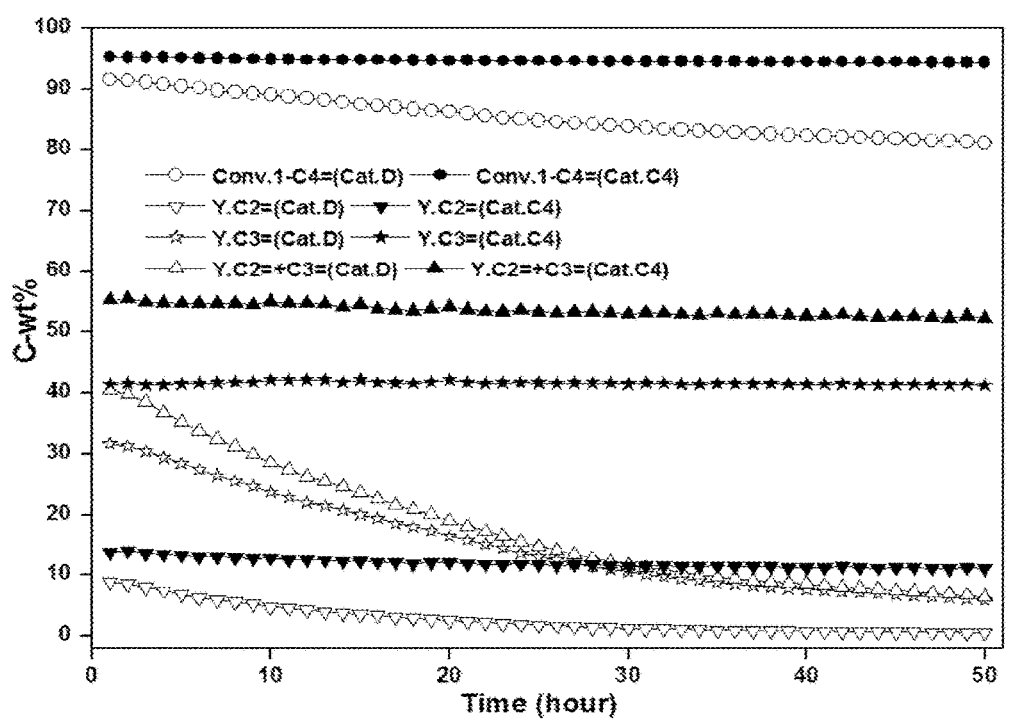
FIG. 4 represents time-on-stream behavior of cracking butene to propylene and ethylene over the core-shell ZSM catalyst (catalyst C4), and the ZSM-5 core (catalyst D).

The results of catalytic performance of 1-butene cracking using parent zeolite as well as modified zeolite catalysts are presented in FIG. 2 and Table 3. Catalyst C4 revealed the highest propylene and ethylene yield (55%), with a P/E ratio of approximately 3, when compared to other catalysts. After surface modification by silica deposition using chemical liquid deposition method, as in catalysts A, B, and C, the propylene and ethylene yield was improved giving a P/E ratio of less than 2. Catalysts D and D1 revealed less activity with a slight increase in the P/E ratio, when compared to the catalyst C4. Kinetics of the conversion reactions of butene to propylene and ethylene over the catalyst C4 and the catalyst D is shown in FIG. 3, wherein concentration of each of the reactants and the products are plotted versus time in a 50-hour time frame. The results as shown in FIG. 3 reveal that the catalyst D deactivates faster than the catalyst C4. More importantly, the yield of propylene and ethylene formation remains unchanged over a period of 50 hours, when catalyst C4 was used, whereas the yield was considerably reduced over the period of 50 hours, when catalyst D was used. The results further represent a greater stability of the core-shell ZSM catalyst (i.e. the catalyst C4) than that of the catalyst D.

hydrothermally treating the ZSM-silicalite mixture to form a hydrothermally treated ZSM-silicalite mixture, and calcining the hydrothermally treated ZSM-silicalite mixture to form a core-shell ZSM catalyst, and contacting a butene-containing hydrocarbon stream with the core-shell ZSM catalyst in a fixed-bed reactor to form a product stream comprising propylene and ethylene, wherein at least 50 wt % of the butene-containing hydrocarbon stream is butene, and wherein the core-shell ZSM catalyst comprises:
  a ZSM-5 core, and
  a silica shell having a thickness in the range of 0.5 to 50 μm, which covers at least a portion of a surface of the ZSM-5 core.

2. The method of claim 1, wherein the silica shell has a thickness in the range of 0.5 to 30 μm.

3. The method of claim 1, wherein the core-shell ZSM catalyst is dispersed in a silica and/or an alumina binder.

4. The method of claim 1, wherein a weight percent of the silica shell in the core-shell ZSM catalyst is within the range of 4 to 75 wt %, with the weight percent being relative to the total weight of the core-shell ZSM catalyst.

5. The method of claim 1, wherein the core-shell ZSM catalyst has an acidity of less than 0.1 mmol/g.

6. The method of claim 1, wherein at least 50 wt % of the product stream is propylene and ethylene.

7. The method of claim 1, wherein a propylene-to-ethylene weight ratio of the product stream is within the range of 0.2 to 4.

8. The method of claim 1, further comprising:
treating the core-shell ZSM catalyst with nitrogen at a temperature in the range of 400 to 700° C. prior to the contacting.

9. The method of claim 1, further comprising:
mixing the butene-containing hydrocarbon stream with nitrogen to form a gaseous mixture prior to the contacting, wherein a partial pressure of the butene-containing hydrocarbon stream in the gaseous mixture is within the range of 5 to 50 psi.

TABLE 3

Products distribution (C-wt %) in cracking of 1-butene using different catalysts at 1 bar, 550° C. (TOS = 1 hr. GHSV = 900 h$^{-1}$).

| | A | A1 | A2 | B | B1 | B2 | C | C1 | C2 | C3 | C4 | D | D1 |
|---|---|---|---|---|---|---|---|---|---|---|---|---|---|
| 1-C$_4$= Conversion | 100.00 | 100 | 98.34 | 100.00 | 100.00 | 97.90 | 98.30 | 97.84 | 97.81 | 96.92 | 95.29 | 91.57 | 92.61 |
| Product distribution (C-wt %) | | | | | | | | | | | | | |
| 1-butene | 0.00 | 0.00 | 1.66 | 0.00 | 0.00 | 2.10 | 1.70 | 2.16 | 2.19 | 3.08 | 4.71 | 8.43 | 7.39 |
| 2-butene | 0.00 | 1.06 | 3.48 | 0.00 | 1.02 | 4.35 | 3.54 | 5.50 | 4.53 | 6.36 | 9.73 | 16.49 | 14.71 |
| Isobutylene | 0.00 | 2.27 | 4.03 | 1.56 | 2.05 | 5.13 | 3.85 | 5.72 | 4.94 | 7.06 | 11.13 | 19.77 | 17.28 |
| C$_2$= | 1.70 | 12.52 | 15.93 | 12.66 | 12.29 | 17.18 | 18.58 | 18.27 | 20.07 | 18.89 | 13.82 | 8.84 | 9.62 |
| C$_3$= | 0.50 | 13.30 | 20.58 | 11.49 | 13.11 | 24.65 | 21.88 | 28.14 | 26.37 | 32.87 | 41.44 | 31.62 | 35.11 |
| C$_4$= | 0.00 | 3.33 | 9.16 | 1.56 | 3.07 | 11.58 | 9.09 | 13.38 | 11.66 | 16.50 | 25.57 | 44.69 | 39.38 |
| C$_5$= | 0.00 | 0.00 | 0.82 | 0.00 | 0.00 | 1.05 | 0.82 | 1.31 | 1.08 | 3.23 | 5.45 | 6.88 | 6.64 |
| C$_6$= | 0.00 | 11.52 | 5.14 | 8.92 | 8.61 | 4.72 | 4.61 | 3.96 | 4.09 | 2.46 | 0.98 | 0.00 | 0.86 |
| Alkanes (C$_1$-C$_6$) | 14.80 | 32.91 | 27.12 | 35.60 | 32.60 | 22.89 | 22.11 | 17.23 | 17.86 | 14.39 | 7.08 | 4.59 | 4.43 |
| Aromatics (BTEX) | 50.50 | 18.75 | 12.96 | 19.67 | 22.71 | 11.35 | 12.46 | 11.15 | 12.23 | 6.33 | 0.00 | 0.00 | 0.00 |
| C$_{8+}$ | 32.60 | 7.68 | 8.29 | 10.10 | 7.60 | 6.58 | 10.44 | 6.56 | 6.64 | 5.33 | 5.68 | 3.38 | 3.95 |
| C$_2$= + C$_3$= | 2.20 | 25.82 | 36.51 | 24.15 | 25.41 | 41.83 | 40.46 | 46.40 | 46.44 | 51.76 | 55.26 | 40.46 | 11.73 |
| P/E ratio | 0.29 | 1.06 | 129 | 0.91 | 1.07 | 1.43 | 1.18 | 1.54 | 1.31 | 1.74 | 3.00 | 3.58 | 3.65 |

The invention claimed is:

1. A method for making a catalyst and cracking a hydrocarbon stream to form propylene and ethylene, comprising:
mixing a ZSM-5 zeolite with a silicalite gel comprising a silicating agent, a structure directing agent, a mineralizing agent, and water to form a ZSM-silicalite mixture, 10. The method of claim 1, wherein the butene-containing hydrocarbon stream is contacted with the core-shell ZSM catalyst at a temperature in the range of 400 to 700° C., and a space velocity in the range of 800 to 10,000 h$^{-1}$.

* * * * *